United States Patent
Coene et al.

(10) Patent No.: US 10,234,384 B2
(45) Date of Patent: Mar. 19, 2019

(54) INSPECTION APPARATUS AND METHOD, LITHOGRAPHIC APPARATUS, METHOD OF MANUFACTURING DEVICES AND COMPUTER PROGRAM

(71) Applicant: ASML Netherlands B.V., Veldhoven (NL)

(72) Inventors: Willem Marie Julia Marcel Coene, Geldrop (NL); Alexander Prasetya Konijnenberg, Rotterdam (NL)

(73) Assignee: ASML Netherlands B.V., Veldhoven (NL)

( * ) Notice: Subject to any disclaimer, the term of this patent is extended or adjusted under 35 U.S.C. 154(b) by 157 days.

(21) Appl. No.: 15/449,367

(22) Filed: Mar. 3, 2017

(65) Prior Publication Data
US 2017/0261428 A1 Sep. 14, 2017

(30) Foreign Application Priority Data
Mar. 8, 2016 (EP) .................................... 16159149

(51) Int. Cl.
*G01N 21/47* (2006.01)
*G01N 21/33* (2006.01)
(Continued)

(52) U.S. Cl.
CPC ............ *G01N 21/47* (2013.01); *G01N 21/33* (2013.01); *G03F 7/70625* (2013.01); *G03F 7/70633* (2013.01); *G03F 9/7092* (2013.01)

(58) Field of Classification Search
CPC .... G01N 21/47; G01N 21/33; G03F 7/70633; G03F 7/70625; G03F 9/7092
USPC ...................................................... 250/372
See application file for complete search history.

(56) References Cited

U.S. PATENT DOCUMENTS 8,115,926 B2   2/2012   Straaijer
2006/0066855 A1   3/2006   Boef et al.
(Continued)

FOREIGN PATENT DOCUMENTS

CN   104345438 A   2/2015
EP   2 053 349 A2   4/2009
(Continued)

OTHER PUBLICATIONS

Frank et al., "Non-interferometric, non-iterative phase retrieval by Green's functions," Journal of the Optical Society of America, vol. 27, No. 10, Oct. 2010; pp. 2244-2251.
(Continued)

*Primary Examiner* — David P Porta
*Assistant Examiner* — Gisselle M Gutierrez
(74) *Attorney, Agent, or Firm* — Sterne, Kessler, Goldstein & Fox P.L.L.C.

(57) ABSTRACT

Disclosed is a method of obtaining data describing an object structure. The method comprising the steps of: (a) illuminating the object structure with illuminating radiation; (b) modulating the phase of the illuminating radiation after scattering by the object structure, the modulation comprising applying a first phase factor dependent upon at least one controllable parameter and an aberration function having a form of a subadditive function of a vector norm; (c) capturing a plurality of intensity patterns, wherein each intensity pattern corresponds to a unique value of the at least one controllable parameter; and (d) reconstructing the data describing the object structure based on the plurality of intensity patterns. Also disclosed are corresponding inspection and lithographic apparatuses, a method of manufacturing devices and a computer program.

18 Claims, 4 Drawing Sheets

(51) Int. Cl.
*G03F 9/00* (2006.01)
*G03F 7/20* (2006.01)

(56) References Cited

U.S. PATENT DOCUMENTS

| | | |
|---|---|---|
| 2011/0102753 A1 | 5/2011 | Van De Kerkhof et al. |
| 2012/0044470 A1 | 2/2012 | Smilde et al. |
| 2012/0218533 A1 | 8/2012 | Lyulina et al. |
| 2013/0181143 A1 | 7/2013 | Betzig et al. |
| 2016/0011523 A1 | 1/2016 | Singh et al. |

FOREIGN PATENT DOCUMENTS

| | | |
|---|---|---|
| EP | 3 032 243 A1 | 6/2016 |
| TW | 2009-25794 A | 6/2009 |
| TW | 2012-43507 A | 1/2012 |

OTHER PUBLICATIONS

Nakajima N., "Noniterative Phase Retrieval from a Single Diffraction Intensity Pattern by Use of an Aperture Array," The American Physical Society, Physical Review Letters, PRL 98, 223901, 2007; pp. 1-4.

Polo A., "Adaptive Optics for EUV Lithography: Phase Retrieval for Wavefront Metrology," University of Turin, 2014; 127 pages.

Gao et al., "Phase-shifting Zernike phase contrast microscopy for quantitative phase measurement," Optical Society of America, Optics Letters, vol. 36, No. 21, Nov. 1, 2011; pp. 4305-4307.

International Search Report and Written Opinion of the International Searching Authority directed to International Application No. PCT/EP2017/053305, dated Apr. 12, 2017; 12 pages.

INSPECTION APPARATUS AND METHOD, LITHOGRAPHIC APPARATUS, METHOD OF MANUFACTURING DEVICES AND COMPUTER PROGRAM

BACKGROUND

Field of the Invention

The present invention relates to inspection apparatus and methods usable, for example, to perform metrology in the manufacture of devices by lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field.

Examples of known scatterometers often rely on provision of dedicated metrology targets. For example, a method may require a target in the form of a simple grating that is large enough that a measurement beam generates a spot that is smaller than the grating (i.e., the grating is underfilled). In so-called reconstruction methods, properties of the grating can be calculated by simulating interaction of scattered radiation with a mathematical model of the target structure. Parameters of the model are adjusted until the simulated interaction produces a diffraction pattern similar to that observed from the real target.

In addition to measurement of feature shapes by reconstruction, diffraction based overlay can be measured using such apparatus, as described in published patent application US2006066855A1. Diffraction-based overlay metrology using dark-field imaging of the diffraction orders enables overlay measurements on smaller targets. These targets can be smaller than the illumination spot and may be surrounded by product structures on a wafer. Examples of dark field imaging metrology can be found in numerous published patent applications, such as for example US2011102753A1 and US20120044470A. Multiple gratings can be measured in one image, using a composite grating target. The known scatterometers tend to use light in the visible or near-IR wave range, which requires the grating to be much coarser than the actual product structures whose properties are actually of interest.

On the other hand, the dimensions of modern product structures are so small that they cannot be imaged by optical metrology techniques. Small features include for example those formed by multiple patterning processes, and/or pitch-multiplication. Hence, targets used for high-volume metrology often use features that are much larger than the products whose overlay errors or critical dimensions are the property of interest. The measurement results are only indirectly related to the dimensions of the real product structures, and may be inaccurate because the metrology target does not suffer the same distortions under optical projection in the lithographic apparatus, and/or different processing in other steps of the manufacturing process. While scanning electron microscopy (SEM) is able to resolve these modern product structures directly, SEM is much more time consuming than optical measurements. Other techniques, such as measuring electrical properties using contact pads is also known, but it provides only indirect evidence of the true product structure.

An alternative type of inspection apparatus uses phase retrieval techniques. Such metrology apparatuses may be used to directly measure product structures which may (for example) comprise aperiodic patterns. Phase retrieval (PR) refers to a class of algorithms that aim to determine the phase information of a complex-valued function, from the information about the measured intensity and some a priori knowledge about the function or its transform. The complexity of the problem is due to the fact that the equations relating the phase and the intensity of an electromagnetic field are non-linear, which makes the phase retrieval problem falling in the class of inverse ill-posed problems.

It would be desirable to provide an improved phase retrieval technique over those already described.

SUMMARY OF THE INVENTION

According to a first aspect of the present invention, there is a method of obtaining data describing an object structure, the method comprising the steps of:

(a) illuminating the object structure with illuminating radiation;

(b) modulating the phase of said illuminating radiation after scattering by the object structure, said modulation comprising applying a first phase factor dependent upon at least one controllable parameter and an aberration function having a form of a subadditive function of a vector norm;

(c) capturing a plurality of intensity patterns, wherein each intensity pattern corresponds to a unique value of the at least one controllable parameter; and (d) reconstructing the data describing the object structure based on the plurality of intensity patterns.

According to a second aspect of the invention, there is provided an inspection apparatus comprising: an illumination optical system operable to illuminate an object structure on a substrate with illuminating radiation; a modulator for modulating the phase of said illuminating radiation after scattering by the object structure, said modulation comprising applying a first phase factor dependent upon at least one controllable parameter and an aberration function having a form of a subadditive function of a vector norm; a detector operable to capture phase modulated radiation subsequent to modulating by said modulator; and a processing unit operable to determine a plurality of intensity patterns, wherein each intensity pattern corresponds to a unique value of the at least one controllable parameter, from the captured phase modulated radiation and to reconstruct data describing the object structure based on the plurality of intensity patterns.

According to a third aspect of the invention, there is provided a method of manufacturing devices wherein object structures are formed on a series of substrates by a lithographic process, wherein properties of the object structures on one or more processed substrates are measured by a method of the first aspect, and wherein the measured properties are used to adjust parameters of the lithographic process for the processing of further substrates.

Other related aspects comprise a computer program product and a lithographic apparatus.

Further aspects, features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
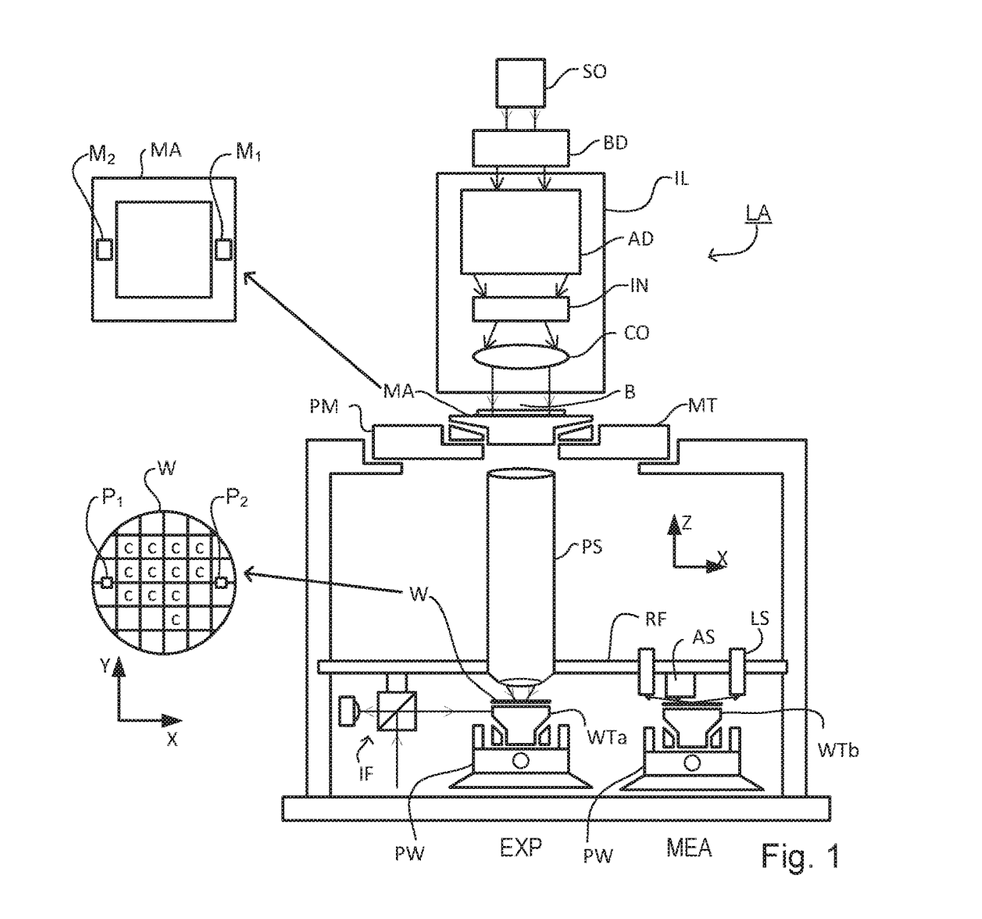
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation. For example, in an apparatus using extreme ultraviolet (EUV) radiation, reflective optical components will normally be used.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support MT may be a frame or a table, for example, which may be fixed or movable as required. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable LCD panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers, is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-) magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
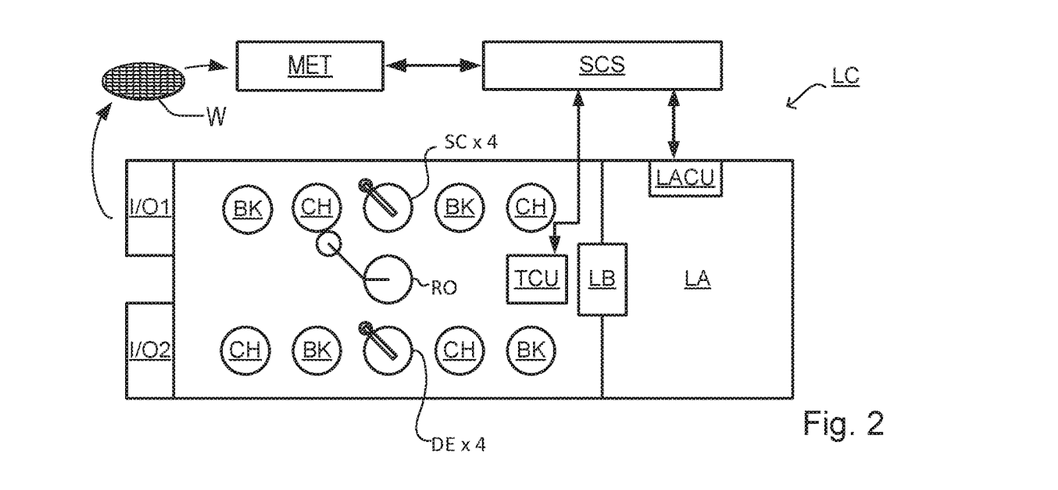
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it may be desirable that the inspection apparatus measure properties in the exposed resist layer immediately after the exposure. However, not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

The metrology step with metrology system MET can also be done after the resist pattern has been etched into a product layer. The latter possibility limits the possibilities for rework of faulty substrates but may provide additional information about the performance of the manufacturing process as a whole.

Any type of product structure may be subject to measurement by the metrology system MET. It will be assumed that the product structures have been formed by optical lithography, using a system of the type described above with respect to FIGS. 1 and 2. The present disclosure is applicable to measurement of microscopic structures formed by any technique, however, not only optical lithography.

Final performance of manufactured device depends critically on the accuracy of positioning and dimensioning of the various features of the product structure through lithography and other processing steps. A product structure made by a real, imperfect, lithographic process may produce a slightly imperfect structure.

Overlay error may cause cutting, contact or other modification to occur imperfectly, or in a wrong place. Dimensional (CD) errors may cause cuts to be too large, or too small (in an extreme case, cutting a neighboring line by mistake, or failing to cut the intended grid line completely). Performance of devices can be influenced by other parameters of lithographic performance, such as CD uniformity (CDU), line edge roughness (LER) and the like. For reasons mentioned above, it is desirable to perform metrology directly on such structures to determine the performance of the lithographic process for CD, overlay and the like.

Figure 3:
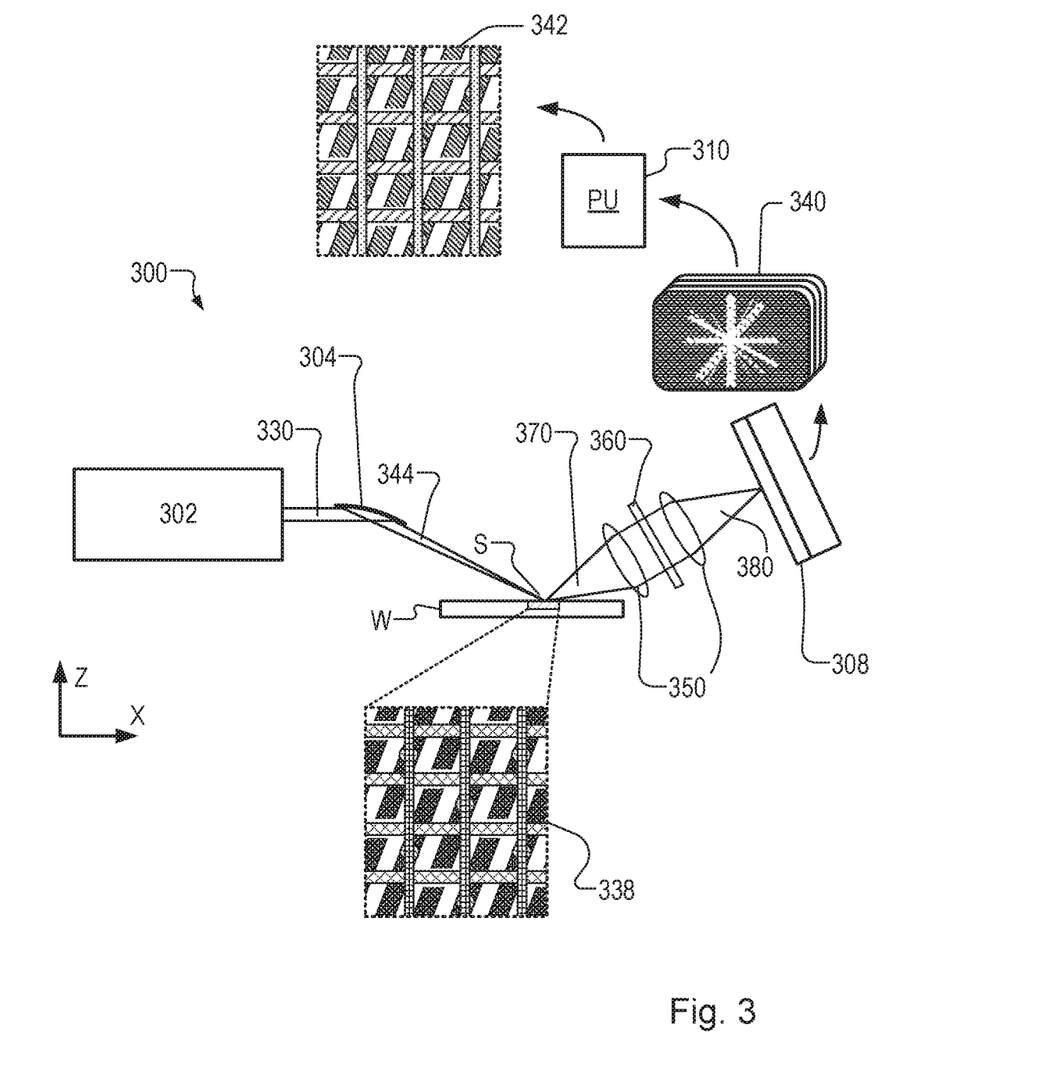
FIG. 3 illustrates schematically an inspection apparatus for obtaining data describing an object structure according to a first embodiment of the invention.

An exemplary inspection apparatus for obtaining data describing an object structure, such as a product structure will now be described with reference to FIG. 3. It will be appreciated that the inspection apparatus 300 may comprise further optical components in addition to those described below; for example, additional imaging optics.

Inspection apparatus 300 comprises a radiation source 302, which emits a beam of illuminating radiation 330. The beam of illuminating radiation 330 may include radiation of a desired wavelength or wavelengths, and may be filtered by an appropriate filtering mechanism. The beam propagates to illumination optical system 304, which focuses the beam of illuminating radiation 330 into a focused beam of illuminating radiation 344. The beam of illuminating radiation 344 should comprise a coherent plane wave, or at least approximately a coherent plane wave. The illumination optical system 304 may be reflective or transmissive; for example, a lens, a two-dimensionally curved mirror or a series of one-dimensionally curved mirrors. The illumination optical system is shown illuminating an object structure 338 (e.g., a product structure) by focusing the radiation beam into a substantially round spot S on the substrate W. In the present example, the object structure 338 is a periodic product structure, although it will of course be appreciated that the exemplary method is applicable to any type of product structure or other microscopic object structure (and may include, for example, product structures comprising periodic patterns, part-periodic patterns and/or aperiodic patterns).

Object structure 338 is in the object plane of an optical arrangement 350 (e.g. lens arrangement). Within a pupil plane of the optical arrangement 350 there is located an optical modulator 360 (e.g., a spatial light modulator) which is operable to modulate the phase of the scattered radiation 370. A detector 308 is located in an image plane of the optical arrangement 350, such that the phase modulated radiation 380 is focused on the detector 308. In the present example, a plurality of intensity patterns (images) 340 are captured by the detector 308, each image being formed by radiation having a unique value of at least one variable parameter of the phase modulated radiation 380. In particular, the at least one variable parameter relates to the phase modulation provided by optical modulator 360. The captured intensity patterns are subsequently transmitted to a processing unit 310.

The recorded intensity patterns 340, and in particular intensity measurements therefrom, are used to reconstruct data representing the object structure 342. In the present example, the reconstruction is performed by using a phase retrieval algorithm. The interaction of the incident radiation with the object structure is characterized by a complex-values reflection function or transmission function, depending on which measurement set-up is being used, being either of reflective or transmissive type.

There are several methods to obtain phase information from intensity measurements, which include:
   Interferometry, where a beam interferes with a known reference beam, thus converting phase information to intensity information which can be measured directly (e.g. holography).
   Iterative algorithms, such as the Gerchberg-Saxton-Fienup-type algorithms, or ePIE (extended ptychographical iterative engine). Using one or several intensity measurements and possibly prior information, iterative algorithms can be used to retrieve phase information from the intensity measurements.
   Transport of Intensity Equation: this is a second-order 2D differential equation that describes how the intensity changes along the optical axis as a function of the lateral phase distribution and intensity distribution. With the appropriate measurement data, this differential equation can solved and the phase information is retrieved.
   Phase contrast microscopy, where the lower frequencies of the Fourier spectrum of the phase-object structure are phase-shifted or removed, so that the phase information can be measured directly as intensity information.
   Focus variation, where a series of through-focus intensity measurements is used to either directly or iteratively reconstruct the amplitude and phase of the object structure.
   2D Astigmatism variation, where the phase of the Fourier spectrum of the object structure is modulated with $2^{nd}$ order 2D astigmatism. The series of intensity measurements are used to reconstruct the amplitude and phase of the object structure directly.

However, each of these methods have their respective drawbacks:
   Interferometry demands experimentally challenging set-ups.
   Iterative algorithms can show problems of stagnation, they can be computationally expensive, there is no proof of convergence to the right solution (convergence to the right solution sometimes depends on the randomly chosen initial guess), sometimes lots of prior information is required for a successful reconstruction.
   Solving the Transport of Intensity Equation requires an approximation of the derivative of intensity along the optical axis, and it requires numerical integration of a two-dimensional second-order differential equation for which appropriate boundary conditions need to be found. Thus, this method requires some approximations, and a computationally expensive procedure.

Phase contrast microscopy is not quantitative and it applies only to pure phase-object structures: if the object structure has an amplitude distribution that differs from its phase distribution, amplitude information and phase information can mix.

Focus variation provides an approximate solution for a direct reconstruction based on the assumption of the Fourier transform of the object structure having a $0^{th}$ order with a high signal amplitude relative to the diffracted orders, so that interference terms between two diffracted orders can be assumed to be negligible.

2D Astigmatism variation requires many intensity measurements to be taken, partly because two parameters need to be varied.

The improved phase retrieval methods described herein provides a more accurate solution for a direct (non-iterative) reconstruction.

To better understand the improved phase retrieval methods, consider that a coherent plane wave is incident on object structure 338 which has a 2D complex valued transmission function φ(R). Here R is a 2D vector in real space. It is an aim of the phase retrieval method to reconstruct φ(R) (i.e. find both its amplitude and phase), using only intensity measurements from the intensity patterns at the detector 340. The object structure 338 is in the object structure plane of optical arrangement 350, and in the back focal plane can be found the Fourier spectrum $\tilde{\phi}$(G) of the object structure 338 having transmission function φ(R) (up to a quadratic phase factor, related to a fixed defocus setting that may occur). Here, G is a 2D vector in the Fourier space of the lens's exit pupil or back focal plane. In the image plane, the intensity I(R) can be measured: I(R)=|φ(R)|². However, the phase of $\tilde{\phi}$(G) can be modulated (e.g. by using modulator 360), for example by multiplying it with a complex-valued phase factor. The complex-valued phase factor may be dependent upon a controllable parameter A, which may comprise a real-valued scalar parameter which can be varied, and a fixed aberration function $f$(G). Such a complex phase factor may take the form of, for example: $e^{i2\pi A f(G)}$. A similar technique is used in phase contrast microscopy. In the previously described example of focus variation, the fixed aberration function may be $f$(G)=|G|², and the controllable parameter A is then the defocus. If $\tilde{\phi}$(G) is modulated by a phase factor $e^{2\pi i A f(G)}$ then detector 308 will measure $I_A(R) = \mathcal{F}\{\tilde{\phi}(G)e^{2\pi i A f(G)}\}|^2$. Alternatively, the complex-valued phase factor may be dependent upon more than one controllable parameter, and its dependency may be more complicated than the simple above case of a parameter A and a single fixed aberration function.

However, instead of choosing the aberration function to be $f$(G)=|G|², it is proposed to choose the aberration function to be of the form:

$$f(G)=h(n(G)), \tag{1}$$

where h(x) is a monotonically increasing subadditive function, and n(G) is a vector norm. A specific set of examples would be f(G)=|G|K, where |G| denotes the Euclidian norm, and K∈(0,1). It can be shown that for such a function, the Fourier transform $\tilde{\phi}$(G) of the object structure φ(R) can be reconstructed (except in the point G=0, i.e. the zeroth order spatial frequency) directly by calculating:

$$\tilde{\phi}^*(0)\tilde{\phi}(G)=\Sigma_n e^{-2\pi i A_n f(G)}\tilde{I}_{A_n}(G) \tag{2}$$

where $\tilde{I}$(G)=$\mathcal{F}$ {I(R)}, and An may comprise a finite set of N parameter values A, which may, for example, be spaced equidistantly by intervals ΔA. Such a reconstruction can be shown to work best for sufficiently small intervals ΔA and sufficiently large ranges NΔA. However, it may be desirable to reduce the number of measurements. This may be achieved by using an appropriate filter H(A) (e.g., a Gaussian function), such that:

$$\tilde{\phi}^*(0)\tilde{\phi}(G)=\Sigma_n H(A_n)e^{-2\pi i A_n f(G)}\tilde{I}_{A_n}(G) \tag{3}$$

Defining:

$$\tilde{\phi}_{recon}(G)=\Sigma_n H(A_n)e^{-2\pi i A_n f(G)}\tilde{I}_{A_n}(G) \tag{4}$$

this equals $\tilde{\phi}^*(0)$ $\tilde{\phi}$(G) except in the case of G=0. The reconstruction can therefore be completed by solving a quadratic equation to calculate for G=0:

$$|\tilde{\phi}(0)|^2 = \frac{-\tilde{\phi}_{recon}(0) + \sqrt{\tilde{\phi}_{recon}^2(0) - 4\sum_{G\neq 0}|\tilde{\phi}_{recon}(G)|^2}}{-2} \tag{5}$$

Figure 4:
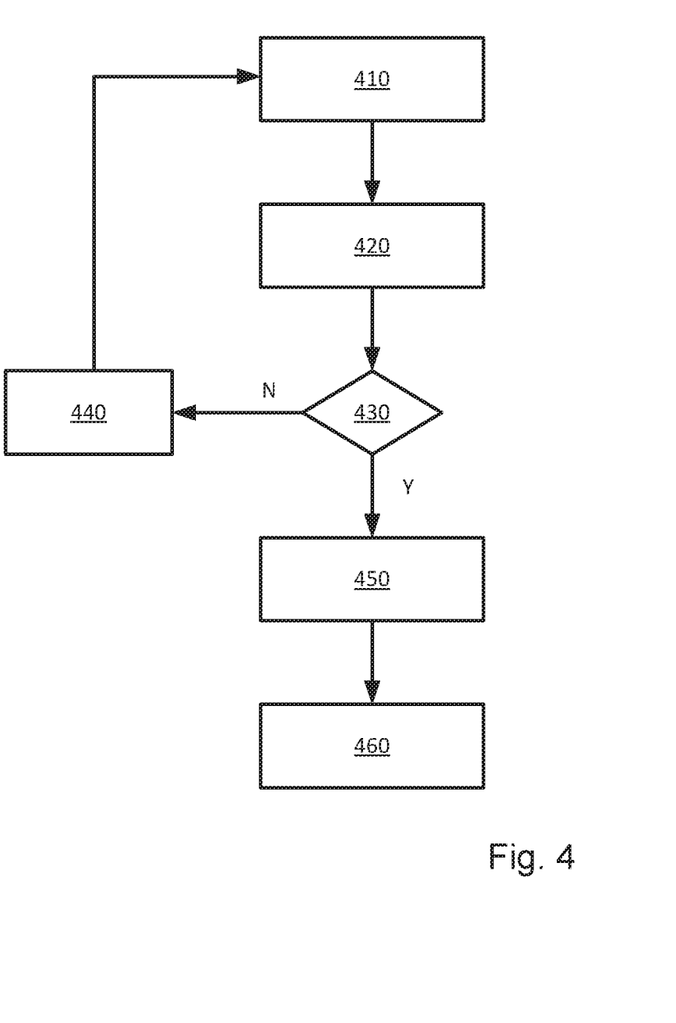
FIG. 4 illustrates a method for obtaining data describing an object using, for example, the apparatus of FIG. 3.

FIG. 4 is a flowchart describing a method according to an embodiment. Such a method may be performed, for example, using an apparatus such as that illustrated in FIG. 3. The method comprises the following exemplary steps:

At step 400, the object structure (e.g., product structure) is illuminated with illumination radiation.

At step 410, the phase of Fourier spectrum $\tilde{\phi}$(G) is modulated according to a function of the form of Equation (1) above.

At step 420, the intensity of the scattered, phase modulated radiation is measured.

At step 430, it is determined whether sufficient (e.g., N) measurements have been performed, each for a different value of parameter A. If not, at step 440, parameter A is varied by a constant interval ΔA and the previous steps are repeated. In an embodiment, the varied parameter A may be a measure of the strength of the phase aberration profile. For example parameter A may comprise the gain of the phase aberration function.

At step 450, after N measurements have been performed, these N (phase modulated) measurements are Fourier transformed, and subsequently they are summed, and multiplied by the phase factor (e.g., $e^{-2\pi i A_n f(G)}$)) to find the Fourier transform of the object structure $\tilde{\phi}$(G) except in G=0. This step may be performed using an appropriate filter (e.g., a Gaussian function).

At step 460, the reconstruction of the object structure described by transmission function φ(R) is completed by the solving of a quadratic equation of the form of Equation (5) to determine the "DC-component" (constant component).

The above example is a conventional plane wave "microscopy" example, where intensity measurements are made in real space (image space). However, the phase retrieval techniques described herein are equally applicable to intensity measurements made in the Fourier space (diffraction space). Such an embodiment may be referred to as a focused-probe coherent diffraction imaging (CDI) embodiment. The only difference is that the roles of real space and Fourier space are swapped. In the microscopy case already described, the Fourier transform (G) of the object structure was multiplied with the phase factor $e^{i2\pi A f(G)}$ and intensity $\tilde{\phi}$(R) measured. By contrast, in the CDI case, it is the object structure φ(R) which is multiplied with a focus-probe $e^{i2\pi A f(R)}$, and the intensity $\tilde{I}$(G) of the far field is measured in Fourier space. In short notation for the CDI-case, the model for the measured image intensity in Fourier space is $\tilde{I}_A(G) = |\mathcal{F}\{\phi(R)p_A(R)\}|^2$ where the phase distribution of the focused probe $p_A(R)$ is given by $e^{2\pi i A f(R)}$.

Figure 5:
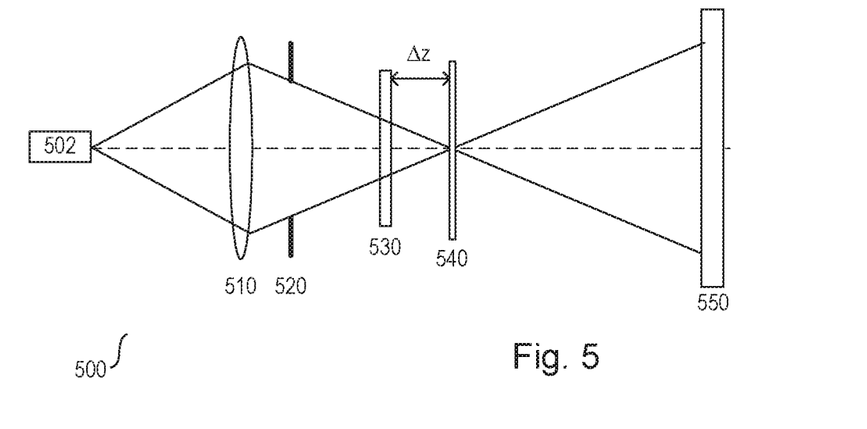
FIG. 5 illustrates schematically an inspection apparatus for obtaining data describing an object structure according to a second embodiment of the invention.

FIG. 5 shows a simplified drawing of such a CDI embodiment. Note, for simplicity, the object structure is shown here as transmissive rather than reflective, although it will be appreciated that the principle is the same. It shows an inspection apparatus 500 comprising radiation source 502, lens 510, aperture 520, object structure 530, modulator 540 and detector 550. Modulator 540 is at the image plane of lens 510. Detector 550 is in the Fourier space and therefore the intensity patterns it captures comprise far-field diffraction patterns. The effective size of the illumination spot formed by the lens is determined amongst others by the defocus value $\Delta z$.

Theory

The derivation of the Equations (1) to (5) is as follows:

It is known that the Fourier transform $\tilde{I}(G)$ of the measured intensity $I(R)$ for a certain value of parameter A is given by the autocorrelation function:

$$\tilde{I}(G; A) = \sum_{G'} \tilde{\phi}^*(G')\tilde{\phi}(G+G')e^{2\pi i A[f(G+G')-f(G')]}$$

Fourier transforming this with respect to A yields:

$$\tilde{\tilde{I}}(G; \omega_A) = \sum_{G'} \tilde{\phi}^*(G')\tilde{\phi}(G+G')\delta[\omega_A - f(G+G') - f(G')]$$

Assuming $f(0)=0$ (which can be assumed without loss of generality, since the phase is defined up to an additive constant), it can be chosen that:

$$\omega_A = f(G)$$

so that the argument of the delta function is 0 for $G'=0$. Calling the argument of the delta function:

$$g(G,G') = f(G) - f(G+G') + f(G')$$

If $g(G,G')$ is 0 only for $G'=0$, then $$\tilde{\tilde{I}}(G;f(G)) = \tilde{\phi}^*(0)\tilde{\phi}(G)$$

which is a direct reconstruction of $\tilde{\phi}(G)$. However, there are three problems A function $f(G)$ has to be found such that $g(G,G')$ only for $G'=0$.

A continuous Fourier transform cannot be performed with respect to A, since only a finite number of measurements with different values for A can be performed.

If $G=0$, the argument of the delta function is 0 for any $G'$, so $\tilde{\phi}^*(0)\tilde{\phi}(G)$ cannot be reconstructed for $G=0$ this way.

Finding $f(G)$

To find a function $f(G)$ such that $g(G,G')$ only for $G'=0$, first consider the aberration function of Equation (1):

$$f(G) = h(n(G)),$$

where $h(x)$ is a monotonically increasing subadditive function for $x \geq 0$ (i.e. $h(a+b) \leq h(a)+h(b)$) for which equality only holds if $a=0$ or $b=0$. $n(G)$ is a vector norm for which by definition the triangle inequality holds:

$$n(G+G') \leq n(G) + n(G')$$

and $$n(G)=0 \Leftrightarrow G=0$$

An example would be:

$$n(G) = \sqrt{(G_x^2 + G_y^2)}$$

and $$h(x) = x^K$$

where $K \in (0,1)$:

$$g(G,G') = h(n(G)) + h(n(G')) - h(n(G+G'))$$

In order to determine for which $G'$ yields $g(G,G)=0$, it is noticed:

$$h(n(G+G')) \leq h(n(G)+n(G')) \text{ (triangle inequality, } h \text{ monotonically increasing)}$$

$$\leq h(n(G)) + h(n(G)) \text{ (}h \text{ is subadditive)}$$

where equality only holds when $n(G)=0$ or $n(G)=0$, and therefore only when $G=0$ or $G'=0$. Thus:

$$g(G,G')=0 \text{ only if } G=0 \text{ or } G'=0 \quad (13)$$

In other words, if $g(G,G')=0$ and $G \neq 0$, then it must hold that $G'=0$. Thus, for all G except $G=0$ the object structure, i.e. amplitude and phase of the wavefield or wavefunction, can be reconstructed.

Sampling a Finite Number of A

Given a finite number of intensity measurements $I(R;A)$, can only be approximated $$\tilde{\tilde{I}}(G; \omega_A = f(G)) \approx \sum_n e^{-2\pi i A_n f(G)} \tilde{I}_{A_n}(G)$$

For a large enough range of A this may give a good reconstruction, but this may require too many measurements to be performed to be practical and/or it may be preferred to reduce the number of measurements. The problem with approximating $\tilde{I}(G; \omega_A = f(G))$ by using a rectangular sampling window as above, is that the delta peak which would be obtained in the case of a continuous Fourier transform with respect to A now becomes a series of sinc functions which have significant sidelobes. Alternatively, should an appropriate filter $H(A)$ (e.g. a Gaussian function) be used:

$$\tilde{\tilde{I}}(G; \omega_A = f(G)) \approx \sum_n H(A_n) e^{-2\pi i A_n f(G)} \tilde{I}_{A_n}(G)$$

such a reconstruction requires fewer intensity measurements $I(R,A)$ to be successful. Note that a peak of finite width (as opposed to the infinitely narrow delta peak) is sufficient, since G is pixelated, and therefore $g(G,G')$ takes on a discrete range of values.

Reconstructing $\tilde{\phi}(G)$ in 0

The above procedure describes how to reconstruct $\tilde{\phi}^*(0)\tilde{\phi}(G)$ for all G except $G=0$.

Thus the calculation of $|\tilde{\phi}(0)|^2$ will complete the reconstruction. To find this value, it should be noted that for the reconstructed $\tilde{\phi}_{recon}(G)$:

$$\tilde{\phi}_{recon}(0) = \Sigma_G |\tilde{\phi}(G)|^2$$

$$\tilde{\phi}_{recon}(G) = \tilde{\phi}^*(0)\tilde{\phi}(G) G=0$$

The first relation comes from the fact that the DC-level of the image intensity equals the total power of the wavefield or wavefunction in Fourier space. Given $\tilde{\phi}_{recon}(G)$, the following can be defined:

$$X = \tilde{\phi}_{recon}(0)$$
$$= \sum_G |\tilde{\phi}(G)|^2$$
$$Y = \sum_{G \neq 0} |\tilde{\phi}_{recon}(G)|^2$$
$$= \sum_G |\tilde{\phi}(G)|^2 |\tilde{\phi}(0)|^2 - |\tilde{\phi}(0)|^4$$
$$= |\tilde{\phi}(0)|^2 X - |\tilde{\phi}(0)|^4$$

The quantity Y gives a quadratic equation for $|\tilde{\phi}(0)|^2$ which can be solved as $$|\tilde{\phi}(0)|^2 = \frac{-X \pm \sqrt{X^2 - 4Y}}{-2}$$

Further, it will be appreciated that the any of the methods described herein may comprise additional method steps. Furthermore, it will be appreciated that the above-described methodology is in essence wavelength independent. In other terms, the above method may be applied using radiation with any wavelength that is suitable for imaging a particular object structure.

In association with the optical system hardware, an embodiment may include a computer program containing one or more sequences of machine-readable instructions defining methods of reconstructing intensity patterns and/or data describing object structures, as well as controlling the inspection apparatus 300, 500 to implement the illumination modes and other aspects of those metrology recipes. This computer program may be executed for example in a separate computer system employed for the image calculation/control process. Alternatively, the calculation steps may be wholly or partly performed within unit PU in the apparatus of FIG. 3 and/or the control unit LACU of FIGS. 1 and 2. There may also be provided a data storage medium (e.g., semiconductor memory, magnetic or optical disk) having such a computer program stored therein.

Further embodiments according to the invention are described in below numbered clauses:

1. A method of obtaining data describing an object structure, the method comprising the steps of:
   (a) illuminating the object structure with illuminating radiation;
   (b) modulating the phase of said illuminating radiation after scattering by the object structure, said modulation comprising applying a first phase factor dependent upon at least one controllable parameter and an aberration function having a form of a subadditive function of a vector norm;
   (c) capturing a plurality of intensity patterns, wherein each intensity pattern corresponds to a unique value of the at least one controllable parameter; and
   (d) reconstructing the data describing the object structure based on the plurality of intensity patterns.

2. A method according to clause 1, wherein the data describing the object structure is a complex-valued wavefield that describes scattering properties of the object structure scattering the illuminating radiation.

3. A method according to clause 1 or 2, wherein the step of reconstructing comprises performing phase retrieval on the intensity patterns.

4. A method according to clause 1, 2 or 3 wherein the step of modulating the phase is performed in Fourier space and the step of capturing a plurality of intensity patterns is performed in real space, said intensity patterns comprising 2D images.

5. A method according to clause 4 wherein said Fourier space corresponds to an exit-pupil of an optical arrangement forming said 2D images.

6. A method according to clause 1, 2 or 3 wherein the step of modulating the phase is performed in real space and the step of capturing a plurality of intensity patterns is performed in Fourier space, said intensity patterns comprising 2D diffraction patterns.

7. A method according to any preceding clause wherein the said unique values of said at least one controllable parameter comprise an equally spaced series of unique values.

8. A method according to any preceding clause wherein said aberration function comprises said vector norm to the power of K, where $K \in (0,1)$.

9. A method according to any preceding clause wherein said vector norm comprises a length.

10. A method according to any preceding clause wherein said step of reconstructing the data comprises summing said plurality of intensity patterns multiplied by a second phase factor corresponding to said first phase factor; and determining a DC component by solving a quadratic equation.

11. A method according to clause 10 wherein the second phase factor is an inverse of the first phase factor.

12. A method according to clause 10 or 11 wherein said summing of said plurality of intensity patterns further comprises applying a filter function.

13. A method according to any preceding clause wherein said controllable parameter comprises a real-valued scalar parameter.

14. A method according to any preceding clause wherein said controllable parameter comprises a gain of said aberration function.

15. An inspection apparatus comprising means for carrying out the method of any of clauses 1 to 14.

16. An inspection apparatus according to clause 15, further comprising:
   an illumination optical system operable to illuminate an object structure on a substrate with illuminating radiation;
   a modulator for modulating the phase of said illuminating radiation after scattering by the object structure, said modulation comprising applying a first phase factor dependent upon at least one controllable parameter and an aberration function having a form of a subadditive function of a vector norm;
   a detector operable to capture phase modulated radiation subsequent to modulating by said modulator; and
   a processing unit operable to determine a plurality of intensity patterns, wherein each intensity pattern corresponds to a unique value of the at least one controllable parameter, from the captured phase modulated radiation and to reconstruct data describing the object structure based on the plurality of intensity patterns.

17. An inspection apparatus according to clause 16, wherein the processing unit is operable to perform phase retrieval on the intensity patterns.

18. An inspection apparatus according to clause 16 and 17 wherein the modulator comprises a spatial light modulator.

19. An inspection apparatus according to clause 16, 17 or 18 wherein the inspection apparatus comprises an optical arrangement to form said intensity patterns as 2D images on said detector, and said modulator is located in an exit-pupil of said optical arrangement.

20. An inspection apparatus according to clause 16, 17 or 18 wherein the inspection apparatus comprises an optical arrangement defining an image plane, and wherein said modulator is located at said image plane, and said detector is located in an exit-pupil of said optical arrangement.

21. A lithographic apparatus comprising an inspection apparatus according to any of clauses 15 to 20.

22. A method of manufacturing devices wherein object structures are formed on a series of substrates by a lithographic process, wherein properties of the object structures on one or more processed substrates are measured by a method according to any of clauses 1 to 14, and wherein the measured properties are used to adjust parameters of the lithographic process for the processing of further substrates.

23. A computer program product comprising machine-readable instructions for causing a processor to perform the reconstructing step (d) of a method according to any of clauses 1 to 14.

24. A lithographic system comprising:
a lithographic apparatus comprising:
   an illumination optical system arranged to illuminate a pattern,
   a projection optical system arranged to project an image of the pattern onto a substrate; and
   an inspection apparatus according to any of clauses 15 to 20,
wherein the lithographic apparatus is arranged to use one or more parameters calculated by the inspection apparatus in applying the pattern to further substrates.

Although specific reference may have been made above to the use of embodiments of the invention in the context of optical lithography, it will be appreciated that the invention may be used in other applications, for example imprint lithography. In imprint lithography, topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of obtaining data describing an object structure, the method comprising:
   illuminating the object structure with illuminating radiation;
   modulating phase of the illuminating radiation after scattering by the object structure, the modulating comprising applying a first phase factor dependent upon at least one controllable parameter and an aberration function having a form of a subadditive function of a vector norm;
   capturing a plurality of intensity patterns, wherein each intensity pattern corresponds to a unique value of the at least one controllable parameter; and
   reconstructing the data describing the object structure based on the plurality of intensity patterns.

2. The method of claim 1, wherein the data describing the object structure is a complex-valued wave-field that describes scattering properties of the object structure scattering the illuminating radiation.

3. The method of claim 1, wherein the reconstructing comprises performing phase retrieval on the intensity patterns.

4. The method of claim 1, wherein:
   the modulating the phase is performed in Fourier space; and
   the capturing a plurality of intensity patterns is performed in real space, the intensity patterns comprising 2D images.

5. The method of claim 4, wherein the Fourier space corresponds to an exit-pupil of an optical arrangement forming the 2D images.

6. The method of claim 1, wherein:
   the modulating the phase is performed in real space; and
   the capturing a plurality of intensity patterns is performed in Fourier space, the intensity patterns comprising 2D diffraction patterns.

7. The method of claim 1, wherein the unique values of the at least one controllable parameter comprise an equally spaced series of unique values.

8. The method of claim 1, wherein the aberration function comprises the vector norm to the power of K, where $K \in (0,1)$.

9. The method of claim 1, wherein the vector norm comprises a length.

10. The method of claim 1, wherein the reconstructing the data comprises summing the plurality of intensity patterns multiplied by a second phase factor corresponding to the first phase factor and determining a DC component by solving a quadratic equation.

11. The method of claim 2, wherein the second phase factor is an inverse of the first phase factor.

12. The method of claim 2, wherein the summing of the plurality of intensity patterns further comprises applying a filter function.

13. The method of claim 1, wherein the controllable parameter comprises a real-valued scalar parameter.

14. The method of claim 1, wherein the controllable parameter comprises a gain of the aberration function.

15. An inspection apparatus comprising:
   an illumination optical system operable to illuminate an object structure on a substrate with illuminating radiation;
   a modulator for modulating the phase of the illuminating radiation after scattering by the object structure, the modulation comprising applying a first phase factor dependent upon at least one controllable parameter and an aberration function having a form of a subadditive function of a vector norm;
   a detector operable to capture phase modulated radiation subsequent to modulating by the modulator; and
   a processing unit operable to determine a plurality of intensity patterns, wherein each intensity pattern corresponds to a unique value of the at least one controllable parameter, from the captured phase modulated radiation and to reconstruct data describing the object structure based on the plurality of intensity patterns.

16. A lithographic apparatus comprising:
an illumination optical system arranged to illuminate a pattern,
a projection optical system arranged to project an image of the pattern onto a substrate; and
an inspection apparatus comprising:
  an illumination optical system operable to illuminate an object structure on a substrate with illuminating radiation;
  a modulator for modulating the phase of the illuminating radiation after scattering by the object structure, the modulation comprising applying a first phase factor dependent upon at least one controllable parameter and an aberration function having a form of a subadditive function of a vector norm;
  a detector operable to capture phase modulated radiation subsequent to modulating by the modulator; and
  a processing unit operable to determine a plurality of intensity patterns, wherein each intensity pattern corresponds to a unique value of the at least one controllable parameter, from the captured phase modulated radiation and to reconstruct data describing the object structure based on the plurality of intensity patterns;
wherein the lithographic apparatus is arranged to use one or more parameters calculated by the inspection apparatus in applying the pattern to further substrates.

17. A method of manufacturing devices, comprising:
forming object structures on a series of substrates by a lithographic process,
measuring properties of the object structures on one or more processed substrates using a method comprising:
  illuminating the object structure with illuminating radiation;
  modulating phase of the illuminating radiation after scattering by the object structure, the modulating comprising applying a first phase factor dependent upon at least one controllable parameter and an aberration function having a form of a subadditive function of a vector norm;
  capturing a plurality of intensity patterns, wherein each intensity pattern corresponds to a unique value of the at least one controllable parameter; and
  reconstructing the data describing the object structure based on the plurality of intensity patterns; and
adjusting, based on the measured properties, parameters of the lithographic process for the processing of further substrates.

18. A computer program product comprising machine-readable instructions for causing a processor to perform operations comprising:
  illuminating the object structure with illuminating radiation;
  modulating phase of the illuminating radiation after scattering by the object structure, the modulating comprising applying a first phase factor dependent upon at least one controllable parameter and an aberration function having a form of a subadditive function of a vector norm;
  capturing a plurality of intensity patterns, wherein each intensity pattern corresponds to a unique value of the at least one controllable parameter; and
  reconstructing the data describing the object structure based on the plurality of intensity patterns.

* * * * *